US009267907B2

(12) United States Patent
Probst et al.

(10) Patent No.: US 9,267,907 B2
(45) Date of Patent: Feb. 23, 2016

(54) MEASUREMENT ARRANGEMENT HAVING ELECTRICALLY HEATED RESISTORS ARRANGED IN GAS PATHS

(75) Inventors: Frank Probst, Herxheim bei Landau/Pfalz (DE); Josef Richter, Karlsruhe (DE)

(73) Assignee: Siemens Aktiengesellschaft, Munich (DE)

( * ) Notice: Subject to any disclaimer, the term of this patent is extended or adjusted under 35 U.S.C. 154(b) by 388 days.

(21) Appl. No.: 13/979,764

(22) PCT Filed: Jan. 18, 2012

(86) PCT No.: PCT/EP2012/050677
§ 371 (c)(1),
(2), (4) Date: Sep. 27, 2013

(87) PCT Pub. No.: WO2012/098138
PCT Pub. Date: Jul. 26, 2012

(65) Prior Publication Data
US 2014/0157866 A1 Jun. 12, 2014

(30) Foreign Application Priority Data
Jan. 20, 2011 (DE) .......................... 10 2011 002 947

(51) Int. Cl.
*G01N 27/04* (2006.01)
*G01F 1/69* (2006.01)
*G01F 1/684* (2006.01)
(Continued)

(52) U.S. Cl.
CPC ............ *G01N 27/046* (2013.01); *G01F 1/6845* (2013.01); *G01F 1/69* (2013.01); *G01F 1/696* (2013.01); *G01N 27/18* (2013.01)

(58) Field of Classification Search
CPC ........... G01F 1/69; G01F 1/692; G01F 1/696; G01F 1/698; G01F 1/6968; G01F 1/6845; G01N 27/046; G01N 27/18
See application file for complete search history.

(56) References Cited

U.S. PATENT DOCUMENTS 3,263,484 A    8/1966  Watson et al.
4,944,035 A    7/1990  Aagardl et al.
(Continued)

FOREIGN PATENT DOCUMENTS

DE    1 473 303 A1    3/1969
DE    102 30 198 A1   1/2004
(Continued)

OTHER PUBLICATIONS

PCT/EP2012/050677 English Translation of WIPO Written Report. Jul. 20, 2013.*
(Continued)

*Primary Examiner* — Lisa Caputo
*Assistant Examiner* — Punam Roy
(74) *Attorney, Agent, or Firm* — Cozen O'Connor

(57) ABSTRACT

A measurement arrangement includes four electrically heated resistors which are arranged in gas paths and are connected to form a Wheatstone bridge, where each of two resistors which are diagonally opposite each other in the Wheatstone bridge are contained in a respective component arranged on a common heated carrier, each respective component is assigned to one heating resistor arranged near the component on the carrier, and where an unbalanced state of the Wheatstone bridge is compensated for by variably energizing the heating resistors.

6 Claims, 1 Drawing Sheet

(51) Int. Cl.
*G01F 1/696* (2006.01)
*G01N 27/18* (2006.01)

(56) References Cited

U.S. PATENT DOCUMENTS

| | | | |
|---|---|---|---|
| 6,928,858 B2 | 8/2005 | Lin | |
| 7,021,136 B2 * | 4/2006 | Vincze | G01F 1/6845 73/204.26 |
| 7,555,944 B2 | 7/2009 | Nakano et al. | |
| 2005/0011260 A1 | 1/2005 | Arndt et al. | |
| 2008/0291966 A1 | 11/2008 | Engel et al. | |
| 2013/0025363 A1 * | 1/2013 | Sato | G01F 1/692 73/204.18 |

FOREIGN PATENT DOCUMENTS

| | | |
|---|---|---|
| DE | 10 2009 014 618 A1 | 8/2010 |
| EP | 0 348 245 A2 | 12/1989 |
| WO | WO 2009/153099 A1 | 12/2009 |

OTHER PUBLICATIONS

Microfabricated thermal conductivity detector for the micro-ChemLab™; Sensors and actuators B: Chemical: International Journal Devoted to Research and Development of Physical and Chemical Transducers, Elsevier S.A. vol. 121, No. 2, pp. 414-422, XP005872220, Paragraph 002., Figures 1, 2.

* cited by examiner

MEASUREMENT ARRANGEMENT HAVING ELECTRICALLY HEATED RESISTORS ARRANGED IN GAS PATHS

CROSS-REFERENCE TO RELATED APPLICATIONS

This is a U.S. national stage of application No. PCT/EP2012/050677 filed 18 Jan. 2012. Priority is claimed on German Application No. 10 2011 002 947.8 filed 20 Jan. 2011, the content of which is incorporated herein by reference in its entirety.

BACKGROUND OF THE INVENTION

1. Field of the Invention

The invention relates to a measurement arrangement having electrically heated resistors that are arranged in gas paths.

2. Description of the Related Art

DE 10 2009 014 618 A1 discloses a heat-conducting detector for use in gas analysis, where two electrically heatable heating filaments that comprise gold or platinum are mounted one behind the other in the middle of a channel such that gas can flow over the heating filaments, and for this purpose are each held at their ends on an electrically-conducting carrier that transverses the channel. In practice, the four heating filaments of two heat-conducting detectors of this type are connected to a Wheatstone bridge, where a measuring gas flows over one heat-conducting detector and a comparison gas or zero gas flows over the other heat-conducting detector and the heating filaments, over which in each case the same gas flows, lie diagonally opposite each other in the Wheatstone bridge.

WO 2009/153099 A1 discloses a microflow sensor, likewise for use in gas analysis, where two electrically heatable grid structures are arranged one behind the other in a gas path. The grid structures can comprise silicon or metal and are connected together with supplementary resistors to a Wheatstone bridge. The supplementary resistors can comprise the grid structures of a further microflow sensor.

In the case of a measurement arrangement disclosed in DE 102 30 198 A1, two electrically heated resistors together with two supplementary resistors are connected in a Wheatstone bridge, where the electrically heated resistors lie diagonally opposite each other and one of the supplementary resistors can be modified for the purpose of balancing the bridge. In order to eliminate offset voltages and slow signal drifts caused by temperature changes, the measuring voltage that is ascertained at the bridge is band-pass filtered.

EP 0 348 245 A2 illustrates a measurement arrangement having an externally-heated temperature-measuring resistor and three supplementary resistors in a Wheatstone bridge, where one of the supplementary resistors can be modified to balance the bridge.

DE 14 73 303 A discloses a measurement arrangement having two heating resistors for heating a measuring substance and a reference substance. The amount of heat absorbed by the respective substance is ascertained using two temperature-measuring resistors in a Wheatstone bridge. The energy supply for the heating resistors is controlled via the measuring voltage ascertained at the bridge.

For accurate measurements, it is important that the ratio of the resistance values of the resistors is identical in each of the two bridge halves. Otherwise, the bridge is out of balance. However, it is difficult to handle micromechanical measurement arrangements such as the known heat-conducting detector or microflow sensor during manufacture. The number of suitable resistors available for selection is limited by manufacturing tolerances and, owing to the sizes of the production batches, by a comparatively small number of available options.

It has been shown to be particularly problematic that the four resistors of the bridge can more or less greatly change over time. In addition, the changes, at least at the beginning, also occur in random directions. In other words, the values of some resistors reduce during the first operating days or weeks, others on the other hand increase. After a comparatively long running-in time, the values of all resistors then start to increase extremely slowly but in a monotone manner, until the resistors are destroyed at the end of their serviceable life. The direction of the changes that occur at the beginning cannot be forecast and therefore in the individual case can lead to the bridge being greatly out of balance for an extremely long period of time even if the bridge is comprised of selected high cost elements.

SUMMARY OF THE INVENTION

It is therefore an object of the invention to render it possible to compensate for the above-described slow unbalancing of a Whitestone bridge and in addition to render it possible for considerably greater fluctuation ranges to be accepted when selecting the resistors or even to render it possible to forego the selection process.

These and other objects and advantages are achieved in accordance with the invention by providing a measurement arrangement having four electrically heated resistors that are arranged in gas paths and are connected to a Wheatstone bridge, where in each case two resistors that lie diagonally opposite each other in the Wheatstone bridge are contained in one component, two components are arranged on a common heated carrier, a heating resistor is allocated in each case to each of the two components, the two components are arranged between the heating resistors lying together with their respective allocated heating resistors in a mirror symmetrical manner with respect to each other on the carrier and where the out-of-balance Wheatstone bridge is compensated for by different currents flowing through the heating resistors.

Based on the temperature level in the bridge circuit being set and held at a constant value by way of the heated carrier, in order to raise the temperature level in the region of the allocated component having the resistors that are contained therein and that lie diagonally opposite to each other in the bridge, current is directed in the case of an out-of-balance bridge through either one or the other heating resistor depending upon the direction of the imbalance. It has been demonstrated that the imbalances of the bridge that generally occur in practice of below one percent with a temperature difference of only a few Kelvin between the components can be completely compensated for, so that commercially available surface mount (SMD) resistors can be used as heating resistors and the required heating capacity is low.

The two components together with the allocated heating resistors are arranged in a mirror-symmetrical manner with respect to each other on the carrier, preferably also in a spot-symmetrical manner. As a result, it is possible to dimension the compensation of the imbalance in an identical manner for the two directions.

The components having the electrically heated resistors arranged therein are preferably heat-conducting detectors or microflow sensors.

Other objects and features of the present invention will become apparent from the following detailed description considered in conjunction with the accompanying drawings.

It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

The measurement arrangement in accordance with the invention is explained with reference to an exemplary embodiment illustrated in the figures of the drawing, in which.

DETAILED DESCRIPTION OF THE PREFERRED EMBODIMENTS

Figure 1:
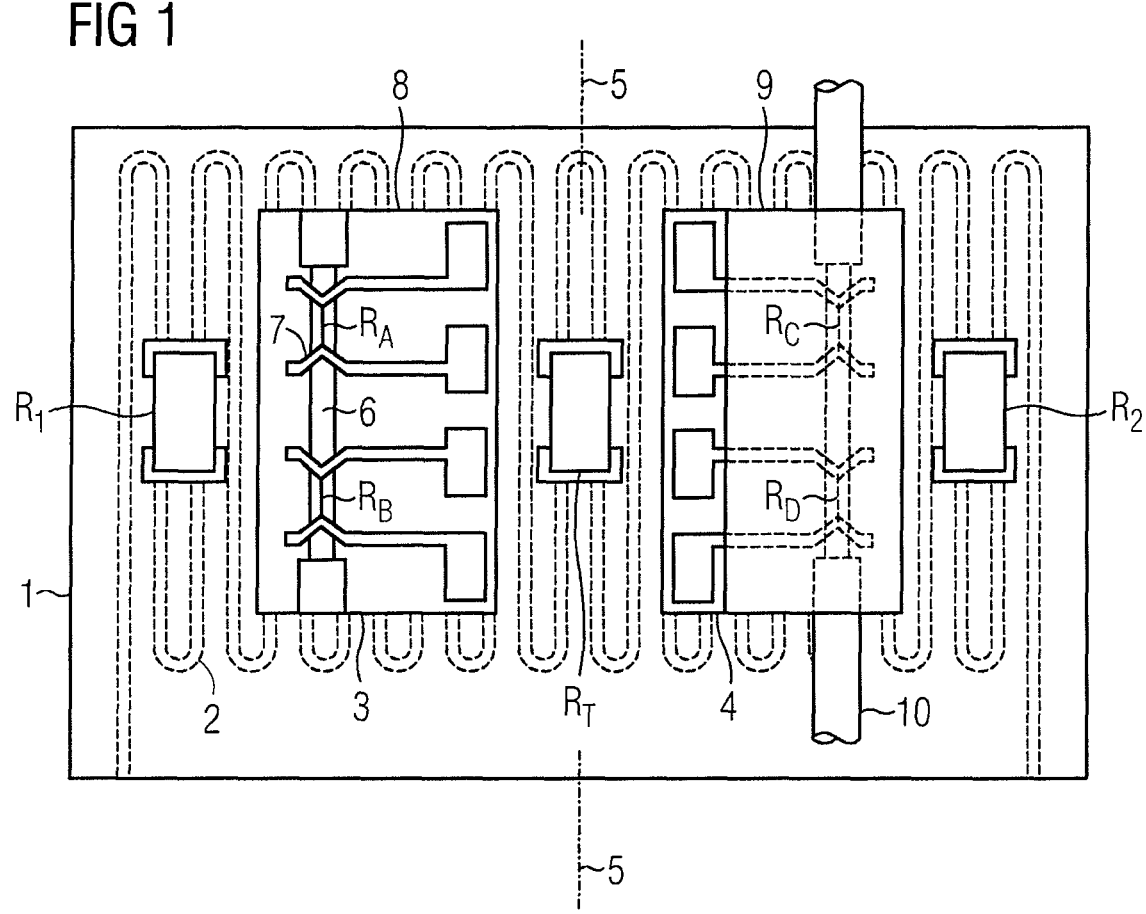
FIG. 1 is a plan view illustration of a measurement arrangement in the form of a heat-conducting detector (HCD)-arrangement with four electrically heatable resistors in accordance with the invention.

FIG. 1 illustrates a plate-shaped carrier 1 comprising an electrically-operated area heater 2 that is arranged therein or on the lower face thereof and comprises a heating coil. Two micromechanically manufactured components (HCD-chips) 3 and 4, two heating resistors $R_1$ and $R_2$ and a temperature measuring resistor $R_T$ are arranged on the upper face of the carrier 1. The heating resistor $R_1$ is arranged in the proximity of the HCD chip 3 and the heating resistor $R_2$ is arranged in the proximity of the HCD chip 4. The HCD chip 3 and the heating resistor $R_1$ lie in a mirror-symmetrical and spot-symmetrical manner with respect to the HCD chip 4 and the heating resistor $R_2$, where the mirror axis 5 extends in the middle of the carrier 1 and the area heater 2, and the temperature measuring resistor $R_T$ lies on the mirror axis 5 in the middle between the HCD chip 3, 4 and the heating resistors $R_1$, $R_2$, respectively.

The two HCD chips 3 and 4 are configured in an identical manner and each comprise a gas path 6 in the middle of which two electrically heatable resistors (heating filaments) $R_A$, $R_B$, and $R_C$, $R_D$, respectively, are each held between two electrically conductive carriers 7 that traverse the gas path 6. A measuring gas flows through the gas path 6 in one HCD chip, such as HCD chip 3, and a comparison gas flows through the other component, for example 4. Each HCD chip 3, 4 comprises a lower carrier plate 8 and an upper carrier plate 9, and the gas path 6, the carriers 7 and the resistors $R_A$, $R_B$, and $R_C$, $R_D$ respectively are embodied or arranged between the plates. For the sake of clarity, the upper carrier plate has been removed from the HCD chip 3. The gases are inlet and discharged by way of capillaries 10 (only illustrated in the case of HCD chip 4).

Figure 2:
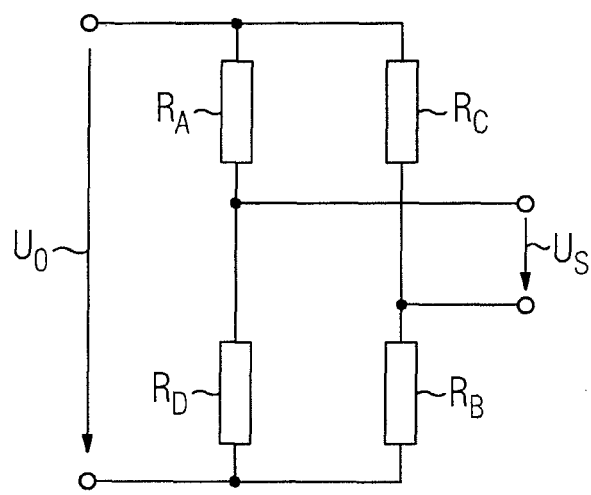
FIG. 2 is an illustration of the connection of the resistors to a Wheatstone bridge in accordance with the invention.

FIG. 2 illustrates the connection of the resistors $R_A$, $R_B$, $R_C$, $R_D$ to a Wheatstone bridge that is supplied with a voltage $U_0$ and generates a measuring or output voltage $U_S$. The resistors $R_A$, $R_B$, and $R_C$, $R_D$ respectively in each case of a HCD chip 3 and/or 4 lie diagonally opposite each other in the bridge.

In order to maintain the measurements comparable with each other over longer periods of time, the Wheatstone bridge is operated in a thermostatically controlled manner, in other words, all four resistors $R_A$, $R_B$, $R_C$ and $R_D$ are held at the same temperature by the area heater 2, the temperature measuring resistor $R_T$ and a controller (not shown). As a consequence and by suitably selecting the resistance values of $R_A$, $R_B$, $R_C$ and $R_D$, it is possible via the bridge circuitry to greatly suppress malfunctions from the supply ($U_0$) and its arrangement of wires.

However, the selection of resistance values is limited by manufacturing tolerances and the number of options available for selection (owing to the sizes of the production batches). Hitherto in practice, still acceptable ratios between $R_A/R_C$ and $R_D/R_B$ respectively have been achieved in the case of +1.5% fluctuation range.

The bridge imbalance: $V=U_S/U_0$ applies in the case of identical measurement conditions on all resistors $R_A$, $R_B$, $R_C$ and $R_D$.

This bridge imbalance V can then be compensated for (in other words, $U_S=0$ V), in that depending upon the direction of the imbalance in addition to the area heater 2 either the heating resistor $R_1$ heats the HCD chip 3 with the resistors $R_A$, $R_B$, to a temperature $T_1$ or the heating resistor $R_2$ heats the HCD chip 3 with the resistors $R_C$, $R_D$ to a temperature $T_2$.

The individual resistors in the bridge obey the following temperature dependency:

$$R_{A,B}=R_{20A,B}(1+\alpha\Delta T_1) \text{ and}$$

$$R_{C,D}=R_{20C,D}(1+\alpha\Delta T_2),$$

where $R_{20}$ represents the resistance value at 20° C., $\alpha$ represents the material-dependent temperature coefficient and $\Delta T=T-20°$ C. represents the temperature difference of the resistor with respect to 20° C.

Based on using the area heater 2 to control the temperature, the following applies:

$$\Delta T_{1,2}=T_{1,2}-20° \text{ C.}=(T_{FH}-20° \text{ C.})+(T_{1,2}-T_{FH}),$$

in other words, the heating output for the heating resistor $R_1$ and/or $R_2$ only needs to produce a temperature increase with respect to the temperature $\Delta T_{FH}$ of the area heater 2.

The imbalance of the bridge is then calculated to be:

$$V = \frac{R_B}{R_B + R_C} - \frac{R_D}{R_A + R_D}$$
$$= \frac{R_{20B}(1+\alpha\Delta T_1)}{R_{20B}(1+\alpha\Delta T_1)+R_{20C}(1+\alpha\Delta T_2)} - \frac{R_{20D}(1+\alpha\Delta T_2)}{R_{20A}(1+\alpha\Delta T_1)+R_{20D}(1+\alpha\Delta T_2)}.$$

Assuming that $\alpha\Delta T_{1,2} \ll 1$, the expression is simplified to:

$$V = \frac{R_{20B}(1+\alpha\Delta T_1)}{R_{20B}+R_{20C}} - \frac{R_{20D}(1+\alpha\Delta T_2)}{R_{20A}+R_{20D}}.$$

It can be further assumed that all four cold resistors are similar, in other words: $R_{20A} \approx R_{20B} \approx R_{20C} \approx R_{20D}$. This further simplifies the expression to:

$$V = \frac{\alpha}{2}(\Delta T_1 - \Delta T_2).$$

If an unavoidable basic imbalance $V_0$ of the bridge is then taken into consideration and attempts are made to compensate for the imbalance, the following relationship is produced:

$$V = V_0 + \frac{\alpha}{2}(\Delta T_1 - \Delta T_2) = 0 \Rightarrow \Delta T_1 - \Delta T_2 = \frac{2V_0}{\alpha}.$$

It is therefore only necessary for current to flow through the heating resistor $R_1$ or $R_2$ depending upon the direction of the imbalance $V_0$ until its power output produces $\Delta T=(\Delta T_1-\Delta T_2)$ which maintains the balance at $2V_0/\alpha$.

In the case of imbalances of $V_0=\pm 0.5\%$ that usually occur in practice and a temperature coefficient $\alpha=4\cdot 10^{-3}$ $K^{-1}$ produces a full compensation with $\Delta T=2.5$ K. The 2.5 K can be achieved with comparatively small electric outputs, so that commercially available SMD resistors can be used for $R_1$ and $R_2$.

In detail, the following advantages are produced:

As the imbalance V reduces, the interference suppression $S=(1-V)$ of the measuring bridge simultaneously greatly increases. As a consequence, when using the HCD-arrangement in a gas analyzer, such as gas chromatographs, the detection limit improves.

It is possible via regular, automatic adjustments to compensate to a great extent for the aging effects of the HCD bridge.

It is possible to omit a pre-selection and pairing of suitable HCD chips, or rather to greatly simplify the pre-selection and pairing process.

As an alternative, it is possible to use a considerably broader value set of HCD chips, which increases the yield in the HCD manufacturing process.

Thus, while there have shown, described, and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements which perform substantially the same function in substantially the same way to achieve the same results are within the scope of the invention. Moreover, it should be recognized that structures and/or elements shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A measurement arrangement, comprising:
a common heated carrier;
a plurality of components arranged on the common heated carrier;
a plurality of electrically heated resistors arranged in gas paths and connected to a Wheatstone bridge, two electrically heated resistors of the plurality of electrically heated resistors that lie diagonally opposite each other in the Wheatstone bridge being arranged in a respective component of the plurality of components; and
a heating resistor allocated to each of the plurality of components, the plurality of components being arranged between heating resistors lying together with their respective allocated heating resistors in a mirror symmetrical manner with respect to each other on the common heated carrier;
wherein different currents flowing through the heating resistors compensate for an imbalance of the Wheatstone bridge.

2. The measurement arrangement as claimed in claim 1, wherein the plurality of components and the allocated heating resistors are arranged together in a mutually spot-symmetrical manner on the carrier.

3. The measurement arrangement as claimed in claim 2, wherein each of the plurality of components with the electrically heated resistors contained therein comprise heat-conducting detectors.

4. The measurement arrangement as claimed in claim 2, wherein each of the plurality of components with the electrically heated resistors contained therein comprise microflow sensors.

5. The measurement arrangement as claimed in claim 1, wherein each of the plurality of components with the electrically heated resistors contained therein comprise heat-conducting detectors.

6. The measurement arrangement as claimed in claim 1, wherein each of the plurality of components with the electrically heated resistors contained therein comprise microflow sensors.

* * * * *